US012727874B2

(12) United States Patent
Fairneny

(10) Patent No.: US 12,727,874 B2
(45) Date of Patent: Sep. 8, 2026

(54) FLEXIBLE SUTURING INSTRUMENT

(71) Applicant: Boston Scientific Scimed, Inc., Maple Grove, MN (US)

(72) Inventor: Ty Fairneny, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 80 days.

(21) Appl. No.: 18/648,864

(22) Filed: Apr. 29, 2024

(65) Prior Publication Data

US 2024/0268815 A1 Aug. 15, 2024

Related U.S. Application Data

(63) Continuation of application No. 16/249,338, filed on Jan. 16, 2019, now Pat. No. 11,992,206, which is a continuation of application No. 13/401,148, filed on Feb. 21, 2012, now abandoned.

(60) Provisional application No. 61/451,366, filed on Mar. 10, 2011.

(51) Int. Cl.

| | |
|---|---|
| ***A61B 17/04*** | (2006.01) |
| *A61B 17/00* | (2006.01) |
| *A61B 17/062* | (2006.01) |
| *A61B 17/29* | (2006.01) |

(52) U.S. Cl.

CPC ...... *A61B 17/0469* (2013.01); *A61B 17/0482* (2013.01); *A61B 2017/00314* (2013.01); *A61B 2017/00323* (2013.01); *A61B 17/0625* (2013.01); *A61B 2017/2927* (2013.01)

(58) Field of Classification Search

CPC ............ A61B 17/0469; A61B 17/0482; A61B 17/0625; A61B 2017/00314; A61B 2017/00323; A61B 2017/2927

See application file for complete search history.

(56) References Cited

U.S. PATENT DOCUMENTS

| | | | |
|---|---|---|---|
| 1,037,864 | A | 9/1912 | Carlson et al. |
| 1,815,725 | A | 7/1931 | Pilling et al. |
| 1,822,330 | A | 9/1931 | Ainslie |
| 3,013,559 | A | 12/1961 | Thomas |
| 3,160,157 | A | 12/1964 | Chisman |
| 3,470,875 | A | 10/1969 | Johnson |

(Continued)

FOREIGN PATENT DOCUMENTS

| | | | |
|---|---|---|---|
| EP | 0589409 | A1 | 3/1994 |
| WO | 9627331 | A1 | 9/1996 |

(Continued)

OTHER PUBLICATIONS

U.S. Appl. No. 16/249,338, filed Jan. 16, 2019, Allowed.

(Continued)

*Primary Examiner* — Phong Son H Dang

(74) *Attorney, Agent, or Firm* — Brake Hughes Bellermann LLP

(57) ABSTRACT

A suturing instrument includes a handle, an elongate shaft, and a suturing head. One or more pull wires extend from the handle into the elongate shaft for controllably deflecting a deflectable portion of the elongate shaft in one or more directions and/or planes for improved maneuverability within the body of a patient during an endoscopic or laparoscopic surgical procedure and for changing the positioning of the suturing head.

18 Claims, 14 Drawing Sheets

(56) References Cited

U.S. PATENT DOCUMENTS 3,638,653 A 2/1972 Berry
3,946,740 A 3/1976 Bassett
3,986,468 A 10/1976 Szostak et al.
4,579,072 A 4/1986 Koike et al.
4,621,640 A 11/1986 Mulhollan et al.
4,802,798 A 2/1989 Adamson
4,890,615 A 1/1990 Caspari et al.
4,909,798 A 3/1990 Fleischhacker et al.
5,059,201 A 10/1991 Asnis
5,289,963 A 3/1994 Mcgarry et al.
5,318,526 A 6/1994 Cohen
5,342,374 A 8/1994 Wan et al.
5,350,385 A 9/1994 Christy
5,364,408 A 11/1994 Gordon
5,381,943 A 1/1995 Allen et al.
5,383,877 A 1/1995 Clarke et al.
5,387,221 A 2/1995 Bisgaard
5,389,103 A 2/1995 Melzer et al.
5,413,272 A 5/1995 Green et al.
5,417,699 A 5/1995 Klein et al.
5,437,682 A 8/1995 Grice et al.
5,447,512 A 9/1995 Wilson et al.
5,447,513 A 9/1995 Davison et al.
5,448,989 A 9/1995 Heckele et al.
5,458,609 A 10/1995 Gordon et al.
5,485,952 A 1/1996 Fontayne
5,496,334 A 3/1996 Klundt et al.
5,497,513 A 3/1996 Arabeyre et al.
5,527,321 A 6/1996 Hinchliffe
5,540,704 A 7/1996 Gordon et al.
5,562,686 A 10/1996 Sauer et al.
5,569,269 A 10/1996 Hart et al.
5,573,542 A 11/1996 Stevens
5,575,800 A 11/1996 Gordon
5,578,044 A 11/1996 Gordon et al.
5,582,615 A 12/1996 Foshee et al.
5,586,986 A 12/1996 Hinchliffe
5,643,294 A 7/1997 Tovey et al.
5,662,664 A 9/1997 Gordon et al.
5,662,666 A 9/1997 Onuki et al.
5,665,096 A 9/1997 Yoon
5,673,841 A 10/1997 Schulze et al.
5,702,754 A 12/1997 Zhong
5,713,910 A 2/1998 Gordon et al.
5,730,747 A 3/1998 Ek et al.
5,746,753 A 5/1998 Sullivan et al.
5,749,828 A 5/1998 Solomon et al.
5,755,727 A 5/1998 Kontos
5,807,241 A 9/1998 Heimberger
5,843,001 A 12/1998 Goldenberg
5,855,585 A 1/1999 Kontos
5,857,964 A * 1/1999 Konstorum .......... A61B 1/0055 600/141
5,860,991 A 1/1999 Klein et al.
5,871,204 A 2/1999 Spirer
5,897,572 A 4/1999 Schulsinger et al.
5,910,148 A 6/1999 Reimels et al.
5,911,727 A 6/1999 Taylor
5,916,146 A 6/1999 Allotta et al.
5,927,162 A 7/1999 Huang
5,951,575 A 9/1999 Bolduc et al.
5,957,937 A 9/1999 Yoon
5,972,000 A 10/1999 Beyar et al.
5,972,013 A 10/1999 Schmidt
5,984,932 A 11/1999 Yoon
5,993,466 A 11/1999 Yoon
6,048,351 A 4/2000 Gordon et al.
6,048,620 A 4/2000 Zhong
6,051,006 A 4/2000 Shluzas et al.
6,059,800 A 5/2000 Hart et al.
6,096,051 A 8/2000 Kortenbach et al.
6,346,111 B1 2/2002 Gordon et al.
6,364,828 B1 4/2002 Yeung et al.
6,454,778 B2 9/2002 Kortenbach
6,551,329 B1 4/2003 Kortenbach et al.
6,592,610 B2 7/2003 Beyar
6,682,493 B2 * 1/2004 Mirigian ............... A61M 25/09 600/585
7,591,783 B2 9/2009 Boulais et al.
8,758,232 B2 6/2014 Graham et al.
9,095,334 B2 8/2015 Kortenbach et al.
9,585,652 B2 3/2017 Kortenbach et al.
2003/0233107 A1 12/2003 Gellman et al.
2004/0034372 A1 2/2004 Chu
2004/0181243 A1 9/2004 Chu et al.
2005/0075538 A1 4/2005 Banik et al.
2005/0131279 A1 6/2005 Boulais et al.
2005/0272978 A1 12/2005 Brunnen et al.
2006/0041263 A1 2/2006 Chu et al.
2006/0159409 A1 7/2006 Sosniak et al.
2007/0270907 A1 11/2007 Stokes et al.
2008/0045333 A1 2/2008 Storch
2008/0109015 A1 5/2008 Chu et al.
2008/0287741 A1 11/2008 Ostrovsky et al.
2008/0300462 A1 12/2008 Intoccia et al.
2010/0121147 A1 5/2010 Oskin et al.
2011/0040308 A1 2/2011 Cabrera et al.
2011/0295242 A1 * 12/2011 Spivey ........... A61B 17/320016 606/1
2013/0340559 A1 * 12/2013 Danitz ..................... B25J 18/06 901/21

FOREIGN PATENT DOCUMENTS

WO 9729694 A1 8/1997
WO 2008045333 A2 4/2008

OTHER PUBLICATIONS

U.S. Appl. No. 13/401,148, filed Feb. 21, 2012, Abandoned.
Communication Pursuant to Rules 161(1) and 162 EPC for EP Application No. 12706761.9, mailed Nov. 4, 2013, 2 pages.
Response to Communication Pursuant to Rules 161(1) and 162 EPC for EP Application No. 12706761.9, filed May 5, 2014, 17 pages.
International Search Report and Written Opinion for International Application No. PCT/US2012/025909, mailed Jun. 6, 2012.

* cited by examiner

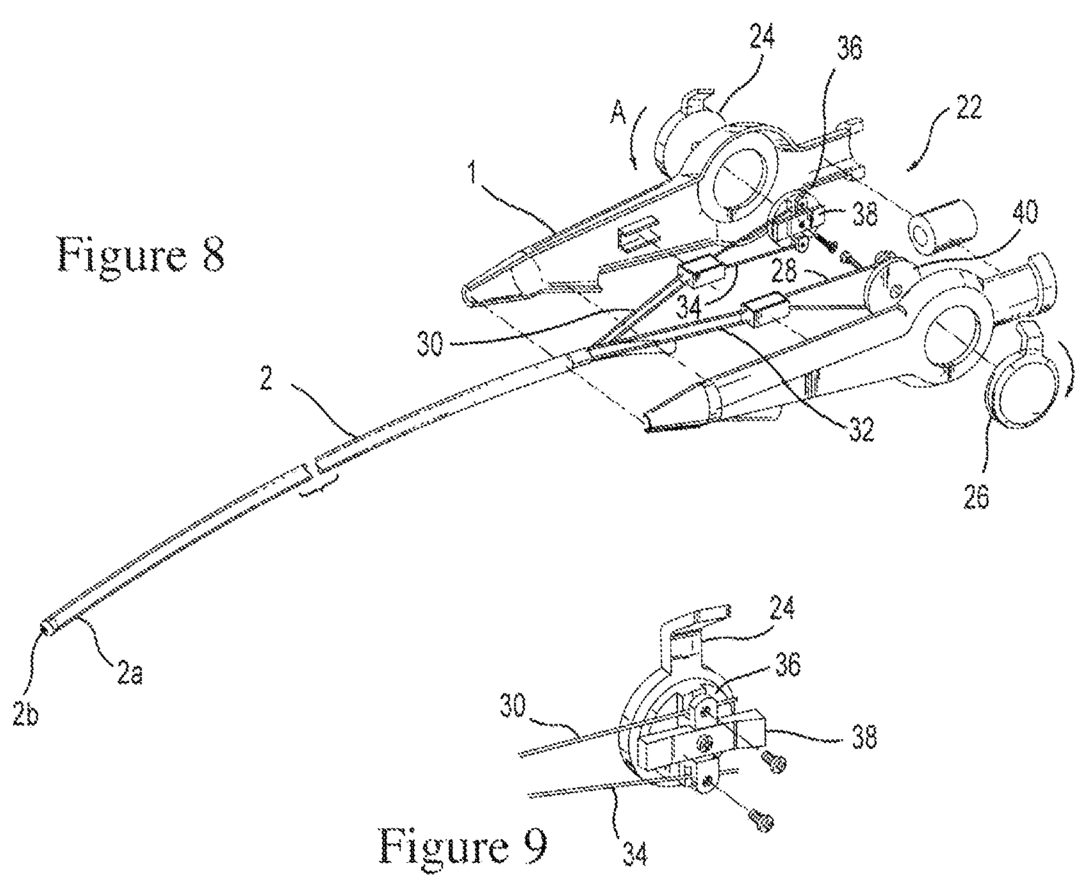
Figure 8
Figure 9
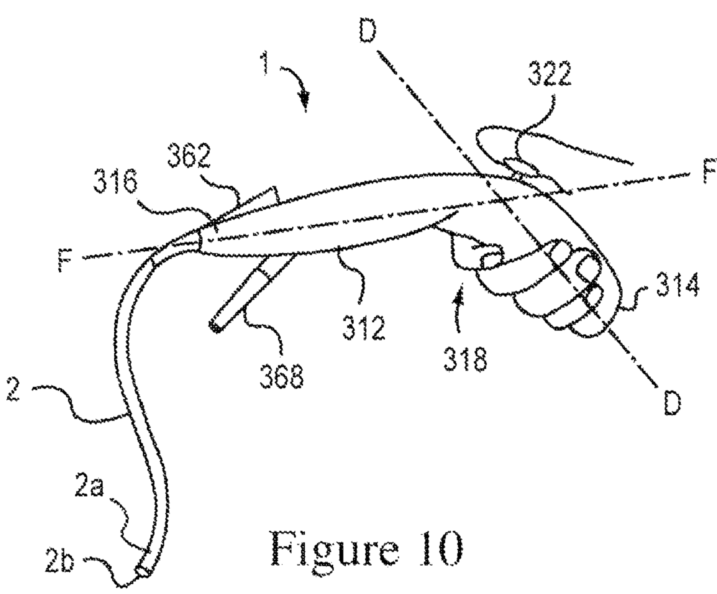
Figure 10

FLEXIBLE SUTURING INSTRUMENT

CROSS-REFERENCE TO RELATED APPLICATIONS

This application is a continuation of, and claims priority to, U.S. patent application Ser. No. 16/249,338, filed on Jan. 16, 2019, entitled "FLEXIBLE SUTURING INSTRUMENT", which claims priority to U.S. patent application Ser. No. 13/401,148, filed on Feb. 21, 2012, entitled "FLEXIBLE SUTURING INSTRUMENT", which claims priority to U.S. Provisional Application No. 61/451,366, filed on Mar. 10, 2011, entitled "FLEXIBLE SUTURING INSTRUMENT", the contents of which are incorporated herein by reference in their entirety.

TECHNICAL FIELD

The invention generally relates to suturing instruments and methods for placing sutures. The suturing instruments of the invention can be used to access difficult-to-reach treatment areas within the body of a patient.

BACKGROUND INFORMATION

Suturing body tissue is a time consuming aspect of many surgical procedures. For many surgical procedures, it is necessary to make a large opening in the human body to expose the area that requires surgical repair. There are instruments available, such as endoscopes, that allow viewing of certain areas of the human body through a small puncture wound without exposing the entire body cavity. Endoscopes can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture a needle and suture. Furthermore, many of the instruments are complicated and expensive to produce due to the numerous parts and/or subassemblies required to make them function properly.

Suturing instruments, and more specifically suturing instruments used in endoscopic procedures, are generally rigid and do not provide the operator a range of motion to access difficult-to-reach parts of the anatomical region requiring sutures. Accordingly, multiple instruments of various configurations and sizes typically are used to access all of the necessary tissue areas. These limitations of known suturing instruments complicate the endoscopic procedure for the surgeon by requiring the insertion and removal of multiple instruments from a surgical site as the target suturing area changes during the course of the surgical procedure.

SUMMARY OF THE INVENTION

The invention generally relates to suturing instruments with improved maneuverability, efficiency and functionality for use during a surgical procedure, such as an endoscopic or laparoscopic procedure. More particularly, the invention is directed to a suturing instrument including a flexible elongate shaft that can be actively deflected. The deflection can be controlled by the user of the instrument (e.g., a surgeon) for improved maneuverability and functionality during a surgical procedure.

In one aspect, the invention relates to a suturing instrument. The suturing instrument includes a handle. An elongate shaft extends from the handle. At least a portion of the elongate shaft is flexible. One or more pull wires extend from the handle into the flexible portion of the elongate shaft for deflecting the flexible portion of the elongate shaft. The suturing instrument further includes a suturing head that extends from a distal end of the elongate shaft. The suturing head includes a needle carrier channel, a needle carrier having a lumen configured to releasably hold/receive the non-penetrating end of a needle, and a needle catch. The needle carrier is movably disposed within the needle carrier channel.

In certain embodiments, a proximal, a middle, and/or a distal portion of the elongate shaft is flexible. In other embodiments, the elongate shaft is flexible along the entire length of the shaft.

Generally, the needle carrier in the suturing head is movably disposed within the needle carrier channel such that it is capable of moving along the needle carrier channel out of the suturing head into an extended position, and back into the suturing head into a retracted position.

The suturing instruments of the invention can further include a needle deployment system at least partially disposed within the elongate shaft. The needle deployment system is coupled to the needle carrier and moves the needle carrier between the extended position and the retracted position. In certain embodiments, the needle deployment system is configured to move the needle carrier out of the suturing head in a semi-circular path towards the needle catch such that the needle held by the needle carrier is released from the needle carrier and retained in the needle catch.

The needle deployment system includes a proximal and a distal end. The distal end of the needle deployment system is coupled to the needle carrier, whereas the proximal end of the needle deployment system is coupled to an actuating mechanism for actuating the needle deployment system. The actuating mechanism is disposed within or on the handle portion of the suturing instrument.

The handle portion of the suturing instruments of the invention can further include a control system coupled to the one or more pull wires for controlling deflection of the flexible portion of the elongate shaft. The control system can include a rotatable cam coupled to the one or more pull wires. Alternatively, the control system can include one or more knobs, hubs or levers attached to the one or more pull wires.

Preferably, at least a portion of the elongate shaft the suturing instruments of the invention is capable of being deflected into multiple different planes relative to a longitudinal axis of the elongate shaft. For example, at least a distal portion of the elongate shaft is capable of being deflected into a plurality of different directions/planes relative to a longitudinal axis of the elongate shaft. Alternatively, the elongate shaft is capable of being simultaneously deflected into multiple different planes along the entire length of the shaft. Deflection of the elongate shaft is actively controlled by a user (e.g., a surgeon) using the one or more pull wires that extend from the handle into a distal portion of the elongate shaft.

In certain embodiments, at least a portion of the elongate shaft includes a flexible coil, such as a Bowden coil. For example, a proximal, a middle and/or a distal portion of the elongate shaft can include a flexible coil. In an alternative embodiment, the flexible coil can extend along the entire length of the elongate shaft. The elongate shaft can further include an outer sleeve disposed on the outside of the flexible coil to provide the instrument with a smooth exterior surface. Deflection of the flexible coil portion of the elongate shaft can be actively controlled by a user (e.g., a surgeon) using the one or more pull wires that extend from the handle into a distal portion of the elongate shaft.

In alternative embodiments, at least a portion of the elongate shaft includes an articulation structure. Preferably, a flexible portion of the elongate shaft includes an articulation structure. For example, a proximal, a middle, and/or a distal portion of the elongate shaft can include an articulation structure. Alternatively, the articulation structure can extend along the entire length of the elongate shaft. Deflection of the articulated portion of the elongate shaft can be actively controlled by a user (e.g., a surgeon) using the one or more pull wires that extend from the handle into a distal portion of the elongate shaft.

In one embodiment, the articulation structure can include a series of stacked links disposed adjacent to one another and movable with respect to each other. Each link includes a front face tapered to a pair of pivot points and a rear face defining a wedge shaped recess for receiving the pivot points of the adjacent link. The one or more pull-wires are configured to provide tension to the articulation structure and hold the adjacent links together.

In another embodiment, the articulation structure includes a first articulation section, the first articulation section and a second articulation section. The first articulation section includes a first series of stacked links disposed adjacent to one another and movable with respect to each other, each link including a front face tapered to a pair of pivot points and a rear face defining a wedge shaped recess for receiving the pivot points of the adjacent link. The second articulation section includes a second series of stacked links disposed adjacent to one another and movable with respect to each other, each link including a front face tapered to a pair of pivot points and a rear face defining a wedge shaped recess for receiving the pivot points of the adjacent link, the wedge shaped recesses of the first articulation section radially offset from the wedge shaped recesses of the second articulation section. The one or more pull wires provide tension to the articulation structure and hold the adjacent links together.

In yet another embodiment, the articulation structure includes a number of ring links, each having an inner circumference and an outer circumference. Each ring link includes: two concave recesses with openings that face radially outward from the outer circumference of the ring link that are positioned on opposite sides of the outer circumference of the ring link; two concave recesses with openings that face radially inward from the inner circumference of the ring link that are positioned on opposite sides of the inner circumference of the ring link and are oriented at 90 degrees to the two concave recesses positioned on opposite sides of the outer circumference of the ring link; and a plurality of spring segments that are secured within the concave recesses on the outer circumferences and inner circumferences of the ring links to join adjacent ring links together and that are bendable in the articulating joint. The concave recesses on the outer circumference of a given ring link are aligned with the concave recesses on the inner circumference of an adjacent ring link in the articulating joint. The spring segments define apertures for receiving the one or more pull wires.

In a second aspect, the invention relates to a suturing instrument having a handle that includes a control system. An elongate shaft extends from the handle. The elongate shaft includes a distal portion. At least a portion of the elongate shaft is flexible. One or more pull wires extend from the handle into the distal portion of the elongate shaft and are coupled to the control system to a user (e.g., a surgeon) to actively control the flexible portion of the elongate shaft. In this second aspect, the suturing instrument further includes a suturing head that extends from a distal end of the distal portion of the elongate shaft. The suturing head includes a needle carrier channel, a need carrier that is configured to releasably receive/hold the non-penetrating tip of a needle, and a needle catch. The needle carrier is movably disposed within the needle carrier channel.

In a third aspect, the invention relates to a suturing instrument that includes a handle. An elongate shaft extends from the handle. The elongate shaft includes a distal portion. At least a portion of the elongate shaft is flexible. In this third aspect, at least a portion of the elongate shaft further includes an articulation structure. One or more pull wires extend from the handle into the distal portion of the elongate shaft. The one or more pull wires are used to control deflection of the articulated portion of the elongate shaft. In this third aspect, the suturing instrument further includes a suturing head that extends from a distal end of the distal portion of the elongate shaft. The suturing head includes a needle carrier channel, a need carrier that is configured to releasably receive/hold the non-penetrating tip of a needle, and a needle catch. The needle carrier is movably disposed within the needle carrier channel.

The embodiments described herein are illustrative only and not intended to be limiting. Instruments or other devices similar or equivalent to those described herein can be used in the practice or testing of the present invention.

BRIEF DESCRIPTION OF THE DRAWING

In the drawings, like structures are referred to by like numerals throughout the several views. Note that the illustrations in the figures are representative only, and are not drawn to scale, the emphasis having instead been generally placed upon illustrating the principles of the invention and the disclosed embodiments. In the following description, various embodiments of the present invention are described with reference to the following drawings.

FIG. 8 is an exploded view a handle of a suturing instrument according to the invention, depicting the components of a control system disposed within the handle.

FIG. 9 is an expanded view of a portion of the control system depicted in FIG. 8.

FIG. 10 depicts an alternative embodiment of a handle including a control system for use in a suturing instrument according to the invention.

DESCRIPTION

Embodiments of the invention are described below. It is, however, expressly noted that the invention is not limited to these embodiments, but rather the intention is that variations, modifications and equivalents that are apparent to a person skilled in the art are also included.

Suturing instruments having a shapeable elongate shaft, an elongate shaft with a preformed bend and/or a passively deflectable suturing head, have been described in U.S. Patent Application Publication Nos. 2004/0181243, 2006/0041263, and 2008/0109015. The present invention provides suturing instruments having flexible elongate shafts that can be controllably deflected by a user (e.g., a surgeon) in a plurality of directions and/or planes, with improved precision and maneuverability over previous designs. The suturing instruments provide a minimally invasive tool that is useful in endoscopic or laparoscopic procedures, particularly in intra-abdominal, intra-vaginal, and rectal procedures, which typically involve difficult-to-reach areas within a body.

Figure 1A:
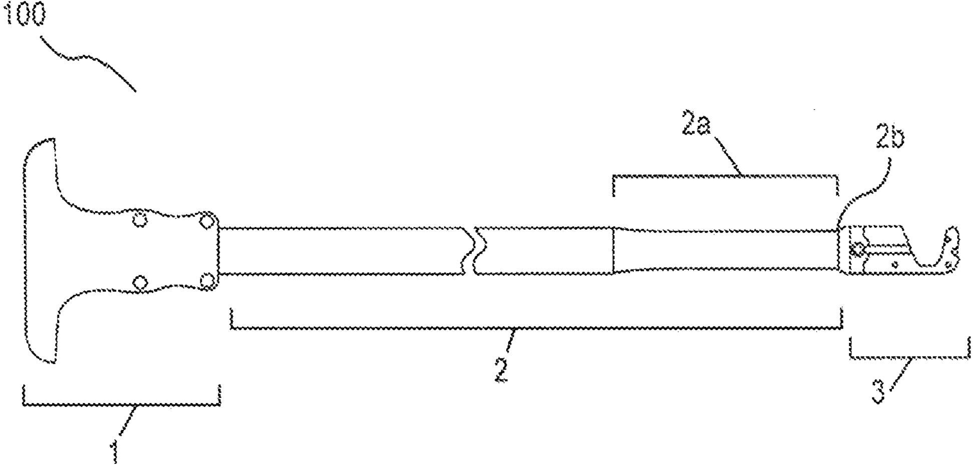
FIG. 1A depicts the general structure of a suturing instrument according to the invention.
Figure 1B:
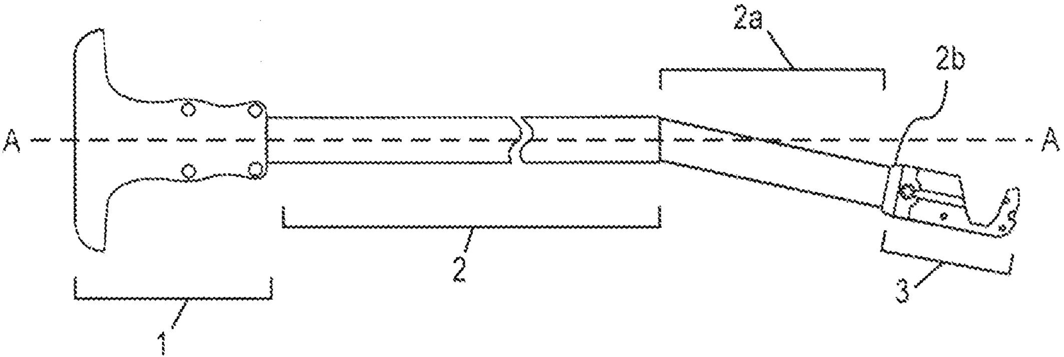
FIG. 1B is a view of the suturing instrument depicted in FIG. 1A that shows the elongate shaft and the suturing head deflected off of a longitudinal axis extending along the suturing instrument.

A flexible suturing instrument according to the invention is used, for example, to access areas within a human body to ligate, fixate, or approximate tissue. The suturing instrument generally throws one or more stitches intracorporeally. FIG. 1A depicts the general structure of a suturing instrument 100 according to an illustrative embodiment of the invention. As shown in FIG. 1A, suturing instrument 100 generally includes a handle 1, an elongate shaft 2 extending from the handle 1 and including a distal portion 2*a*, and a suturing head 3 extending from a distal end 2*b* of the distal portion 2*a* the elongate shaft 2. At least a portion of the elongate shaft is adapted to be flexible such that it can be deflected in one or more directions and/or planes relative to a longitudinal axis extending along the elongate shaft. For example, the distal portion 2*a* of the elongate shaft 2 is adapted to be flexible such that it can be deflected off of a longitudinal axis A extending along the suturing instrument (FIG. 1B). Alternatively, the entire length of the elongate shaft 2 is adapted to be flexible such that portions of the shaft can be deflected in one or more directions and/or planes relative to the longitudinal axis A extending along the suturing instrument.

One or more cables or pull wires extend from the handle 1 into the distal portion 2*a* of the elongate shaft 2 and are configured for actively controlling deflection of the flexible portion of elongate shaft 2 relative to a longitudinal axis extending along the length of the elongate shaft 2. The one or more cables or pull wires can extend from the handle 1, within the elongate shaft 2, and into the distal portion 2*a*. Alternatively, the one or more cables or pull wires can extend from handle, along the outside of elongate shaft 2, and into the distal portion 2*a*. In certain embodiments, the one or more pull wires terminate in the distal portion of the shaft, but the wires can terminate elsewhere such as in the suturing head 3.

In certain embodiments, at least a portion of elongate shaft 2 includes a flexible coil, such as a Bowden coil. For example, the distal portion 2*a* of the elongate shaft can include a flexible coil. Alternatively, the entire length of the elongate shaft 2 can include a flexible coil. The flexible coil can be passively and/or actively bent into one or more shapes. For example, the flexible coil can passively conform to the shape of a bodily passage during insertion into the passageway. The flexible coil instead can be actively bent into a shape by a user's hand(s) prior to insertion into a bodily passage or cavity, such that the shaft 2 retains that shape during use. The flexible coil will be stiffer in embodiments where physical manipulation of the coiled portion of the shaft 2 result in that portion of the shaft 2 retaining its modified shape (such as an "S" shape). The stiffer the flexible coil, the harder it is to bend, but the more it will resist changing from its bent shape. The one or more pull wires extending from the handle 1 into the distal portion 2*a* of the elongate shaft instead can be used to actively control deflection of the flexible coil portion of the shaft 2.

In alternative embodiments, at least a portion of the elongate shaft 2 includes an articulation structure that forms an articulated portion of the shaft 2 and allows the articulated portion to be controllably deflected by the one or more pull wires extending from the handle 1. For example, the distal portion 2*a* of the elongate shaft can be articulated and thus controllably deflected in one or more planes relative to the longitudinal axis of the elongate shaft 2 using the one or more pull wires extending from the handle 1 to the distal portion 2*a* of the shaft 2. Alternatively, the entire length of the elongate shaft 2 can include an articulation structure that enables the entire length of the elongate shaft 2 to be actively and controllably deflected in one or more planes relative to the longitudinal axis of the elongate shaft 2 using the one or more pull wires. Examples of articulation structures suitable for use with the suturing instruments of the invention are described in detail below.

A flexible outer sleeve can be placed over the flexible coil portion and/or the articulated portion of the elongate shaft to provide a smooth exterior surface. The outer sleeve can be made from soft, thin polyurethane, LLDPE, silicon, pellethane, polyurethane, or other approved biocompatible materials such as polyethylene, polypropylene or polyvinyl alcohol. Additionally, the outer sleeve can be coated with a hydrophilic, lubricious coating such as HYDROP ASS™ hydrophilic coating available from Boston Scientific Corporation, of Natick, Mass., and described in U.S. Pat. Nos. 5,702,754 and 6,048,620, which are herein incorporated by reference in their entireties. Additionally, the outer sleeve can be coated with a drug agent to treat internal body tissues.

Figure 2:
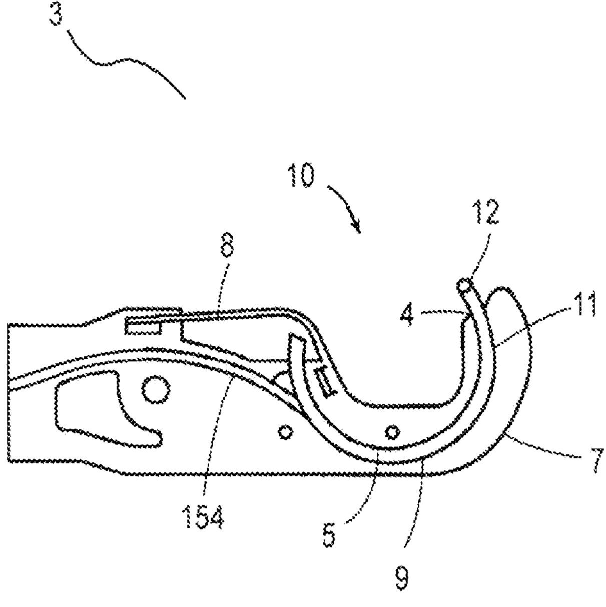
FIG. 2 illustrates a suturing head for use in a suturing instrument according to the invention.

Turning now to the suturing head components of the suturing instruments of the invention, an exemplary embodiment of the suturing head 3 is depicted in FIG. 2. As shown in FIG. 2, suturing head 3 defines an opening or needle exit port 4 through which a needle carrier 5 advances a needle 6 that is releasably held within needle carrier 5. Suturing head 3 includes a curved portion 7, needle carrier 5, and a needle catch 8. The curved portion 7 defines a needle carrier channel 9, which ends at needle exit port 4. The curved portion 7 also defines an opening 10 for receiving tissue. Needle carrier 5 is movably disposed within needle carrier channel 9 in the curved portion 7 such that needle carrier 5 is capable of moving out of the suturing head into an extended position, and back into the suturing head into a retracted position. A distal portion 11 of the needle carrier 5 defines a lumen 12 dimensioned for holding/receiving the nonpenetrating end of the needle 6. Preferably, the needle carrier 5 is configured to move out of suturing head 3 in a semi-circular path towards needle catch 8, such that needle 6 is released from needle carrier 5 and retained in needle catch 8. However, it should be noted that the exact structure and operation of the suturing head 3 can vary based on the type of head used.

Figure 3:
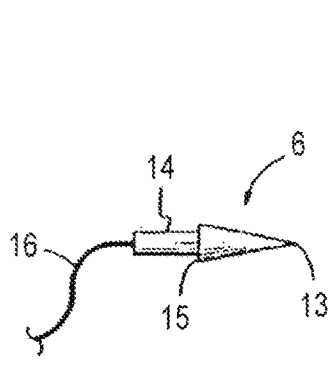
FIG. 3 depicts an example of a needle for use in a suturing instrument of the invention.
Figure 4:
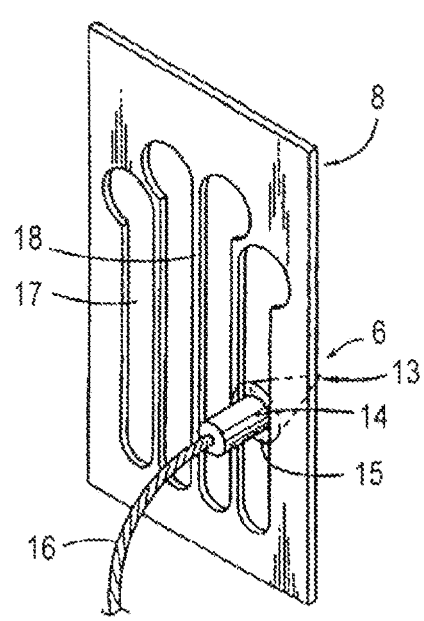
FIG. 4 depicts an example of a needle catch for use in a suturing instrument according to the invention.

Referring now to FIG. 3, the needle 6 includes a tissue penetrating tip 13 and a shaft 14 coupled to the tip 13, thereby forming shoulder 15. The shaft 14 is coupled to a suture 16. The needle 6 is inserted into lumen 12 of needle carrier 5 and held by a slight friction fit. Referring now to FIG. 4, needle catch 8 includes one or more openings 17 defined by successive ribs 18. Needle catch 8 receives tip 13 of needle 6 (coupled to suture 16) through opening 17, the ribs 18 deflect slightly to allow needle 6 to pass through. After the formed shoulder 15 of needle 6 has passed ribs 18, the ribs 18 spring back to their original position defining the openings 17 and needle 6 remains captured in needle catch 8. It should be noted that the needle 6 and needle catch 8 shown are merely one possible type and other designs may be selected.

Suturing instrument 100 further includes a needle deployment system that is disposed in at least a portion of the elongate shaft 2 and coupled to needle carrier 5 for moving the needle carrier 5 between the extended and retracted positions. Various configurations and components of needle deployment systems suitable for use in the suturing instruments of the invention are described in U.S. Pat. No. 5,713,910 to Gordon et al., U.S. Pat. No. 5,578,044 to Gordon et al., U.S. Pat. No. 5,575,800 to Gordon, U.S. Pat. No. 5,540,704 to Gordon et al., U.S. Pat. No. 5,458,609 to Gordon et al., and U.S. Pat. No. 5,364,408 to Gordon, all of which are incorporated herein by reference in their entireties. In an exemplary embodiment, the needle deployment system extends longitudinally through the elongate member 2 to the suturing head 3 where a distal portion 19 of the needle deployment system is coupled to needle carrier 5 within the suturing head 3 (FIG. 6).

The handle component 1 of suturing instrument 100 can include an actuating mechanism 110 that is disposed within the handle 1 and coupled to a proximal portion of the needle deployment system for actuating the needle deployment system. In the illustrative embodiment depicted in FIG. 5, the actuating mechanism 110 includes an actuator button 117 and a shaft 116 (together 112). The actuating mechanism 110 is coupled to a bearing 118, a hole 121, a button end 119, and a wireform 103. The bearing 118 rides along a surface 105 that is formed by the inside of the elongate shaft 2. The wireform 103 is inserted into the hole 121, coupling it to the actuator button 117. A spring 115 encircles the wireform 103, abuts the button end 119, and is compressed between the button end 119 and a spring washer 113.

Figure 5:
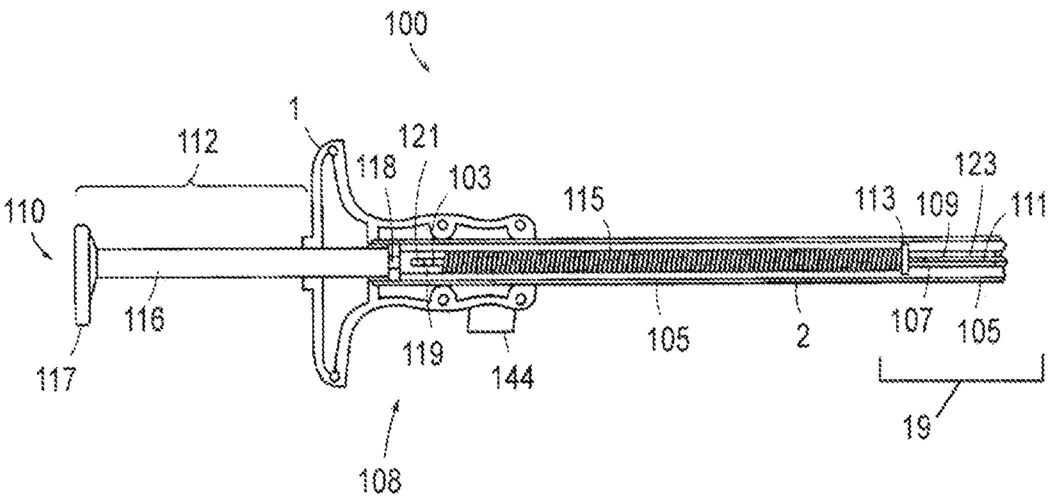
FIG. 5 depicts an example of a handle coupled to an elongate shaft of a suturing instrument according to the invention, and shows an example of an actuating mechanism that is disposed within the handle and coupled to a needle deployment system that is partially disposed within the elongate shaft.

The distal portion 19 of the needle deployment system depicted in FIG. 5 includes the spring washer 113, a center tube 107, a pusher wire 111, and a guidance sleeve 109. The spring washer 113 is seated upon the center tube 107. The center tube 107 is housed by the surface 105 and is constrained in the distal portion 106 of the suturing instrument 100. The pusher wire 111 is attached to the wireform 103 by means of a weld, a crimp, a coupling, adhesive, or other means, and is slideably disposed within the guidance sleeve 109, the sleeve 109 being disposed within a surface 123 formed by the inside diameter of the center tube 107. In one embodiment, the pusher wire 111 is constructed of a shape memory material, for example, a nickel titanium alloy such as Nitinol™. Preferably, the shape memory material is chosen for its combination of properties that allow for bendability and high column strength when constrained.

Figure 6:
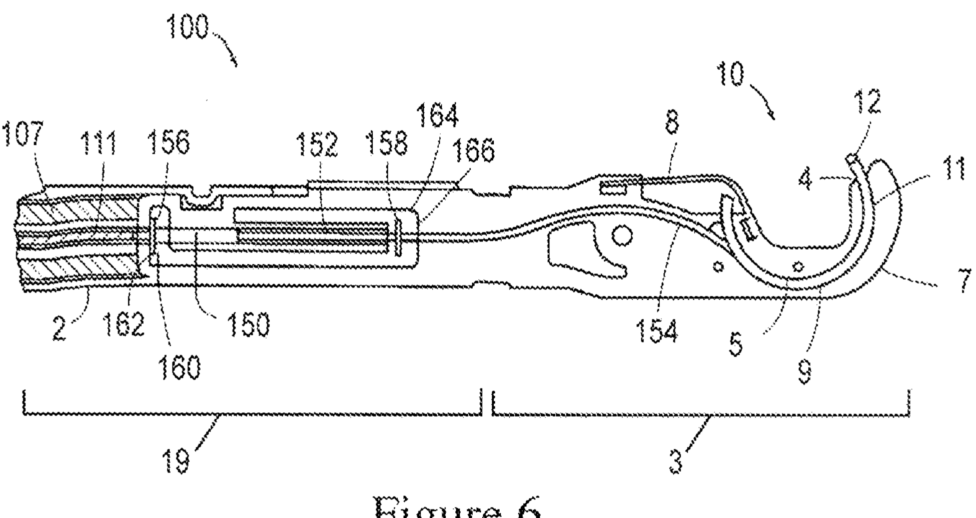
FIG. 6 is a cross-sectional view of a distal portion of a suturing instrument according to the invention depicting a needle deployment system coupled to a needle carrier disposed within a suturing head.
Figures 7A, 7B, 7C, 7D, 7E, 7F, 7G:
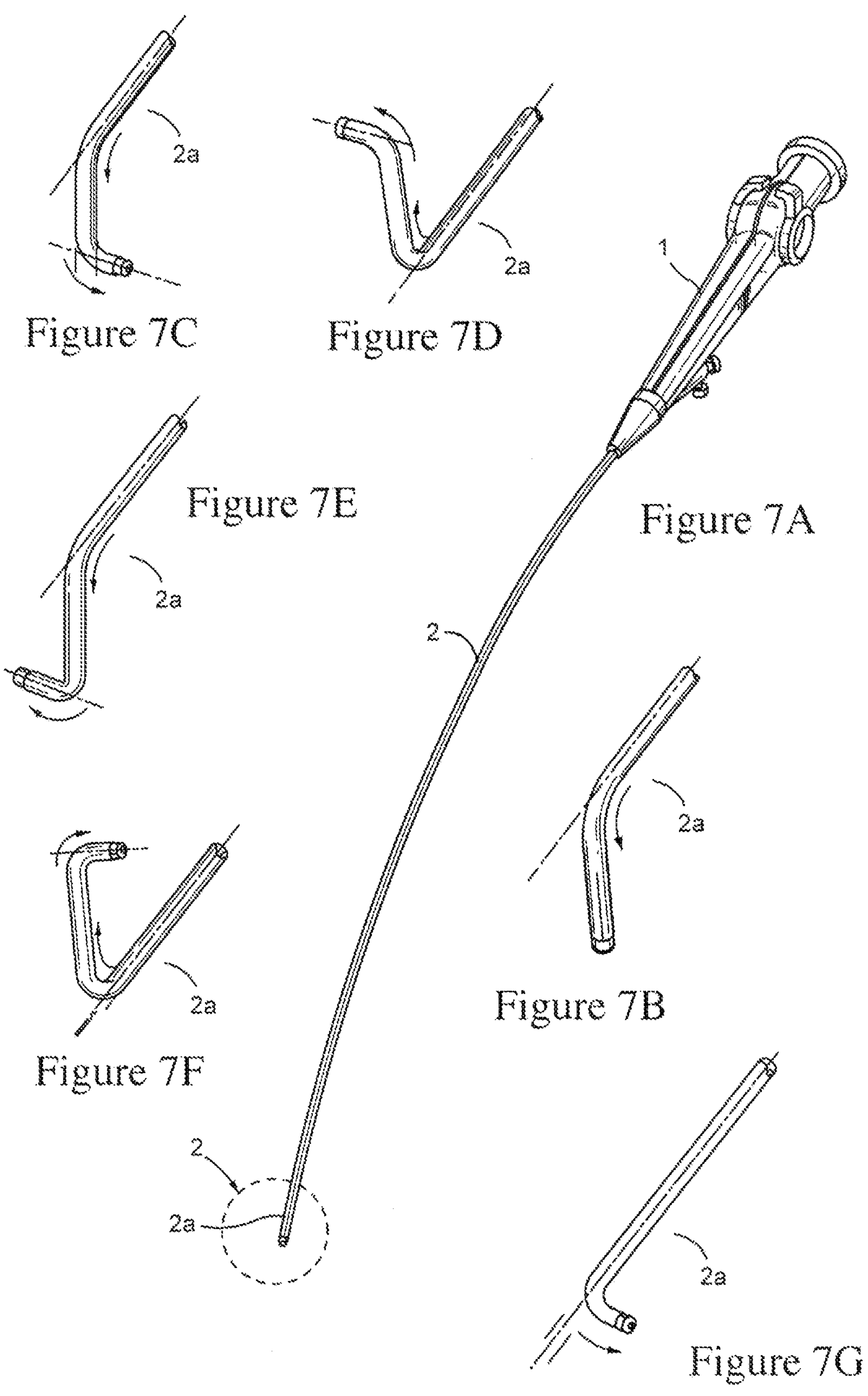
FIGS. 7A-7G depicts a suturing instrument having a flexible distal portion, and the multiple different directions and/or planes in which the distal portion can be bent or deflected.

Referring now to the illustrative embodiment depicted in FIG. 6, the distal portion of the suturing instrument 100 depicted in FIGS. 1 and 5 includes the distal portion **2*a* of the elongate shaft 2 and a distal portion of the needle deployment system 19 coupled to the needle carrier within suturing head 3. The distal portion of the needle deployment system depicted in FIG. 6 includes the pusher wire 111, a backstop washer 156, a pocket 160 that includes a back wall 162, a coupling 150, a track 152, a downstop washer 158, a pocket 164 that includes a wall 166, and a carrier wire 154. The pusher wire 111 of the needle deployment system is attached by welding or other means to the coupling 150, which is slideably disposed within the track 152. The coupling 150 is attached to the carrier wire 154, which by virtue of its attachment to the coupling 150 is also slideably disposed within the track 152. The carrier wire 154 is mechanically coupled to the extendable needle carrier 5 by means of a weld, a coupling, adhesives, or other means. The coupling 150 abuts the backstop washer 156 that is slideably disposed about the pusher wire 111 and is contained within the pocket 160 that includes the back wall 162, against which the backstop washer 156 rests. The track 152 terminates distally in the pocket 164 that includes the wall 166. The downstop washer 158 is slideably disposed about the carrier wire 154 and constrained within the pocket 164**.

Referring again to the handle component of the suturing instruments of the invention, handle 1 of the suturing instrument 100 can further include a control system coupled to the one or more pull wires for actively controlling deflection of the flexible portion of the elongate shaft. Various configurations of handles that include a control system coupled to one or more pull wires for controllably deflecting an elongate shaft of an endoscopic medical device, or a portion thereof, are described in U.S. Patent Application Publication No. 2008/0300462 and 2010/0121147, the contents of which are incorporated herein by reference in their entireties.

One illustrative embodiment of a handle configuration that includes a control system and is suitable for use in the suturing instruments of the invention is depicted in FIG. 8 and FIG. 9. As shown in FIGS. 8 and 9, the handle 1 includes a control system 22 to actively control the deflection of the distal portion 2*a* of the elongate shaft 2. In the illustrated embodiment, the control system 22 comprises two activation hubs (rotatable cams) 24, 26, and four pull wires 28, 30, 32, 34. Each activation hub 24, 26 is connected to two of the pull wires and allows the user (e.g., a surgeon) to manipulate the distal portion 2*a* of the elongate shaft 2 in one plane of deflection. Additional activation hubs and/or pull wires could be included in the control system 22 depending on how many planes of deflection are desired. The pull wires 28, 30, 32, 34 are made from stainless steel, polymer filaments, or other metals and alloys such as, for example, Nitinol™.

The first activation hub 24 is movably attached to the right side of the handle 20 from the perspective of the user and includes a floating cam 36 and a cam stop 38. The proximal ends of pull wires 30 and 34 are connected to the floating cam 36. When the user rotates the first activation hub 24 in a clockwise direction, as indicated by line A on FIG. 9, tension is applied to pull wire 34, and tension is released from pull wire 30, thereby deflecting the distal portion 2*a* of the elongate shaft 2 to the left. Conversely, when the user rotates the first activation hub 24 in the opposite, counterclockwise direction, tension is applied to pull wire 30 and tension is released from pull wire 34, thereby deflecting the distal portion 2*a* to the right.

The user can achieve up and down deflection of the distal portion 2*a* of elongate shaft 2 by rotating the second activation hub 26 in a similar manner. The second activation hub 26 is movably attached to the left side of the handle 1 from the perspective of the user and includes a floating cam 40 and a cam stop (not shown). The proximal ends of pull wires 28 and 32 are connected to floating cam 40. When the user rotates the second activation hub 26 in a clockwise direction as indicated by line Bon FIG. 9, tension is applied to pull wire 28, and tension is released from pull wire 32, thereby deflecting the distal portion 2*a* in an upward direction. Conversely, when the user rotates the second activation hub 26 in the opposite, counterclockwise direction, tension is applied to pull wire 32 and tension is released from pull wire 28, thereby deflecting the distal portion 2*a* in a downward direction. The control system 22 could comprise additional components or alternative means for achieving defection of the distal portion 2*a* of the elongate shaft 2.

The handle/control system can be used to deflect the flexible portion of the elongate shaft in one or more directions and/or planes relative to a longitudinal axis extending along the shaft. The control system can also be used to simultaneously deflect two or more portions of the elongate shaft in different planes relative to the longitudinal axis. For example, the control system can be used to deflect the distal portion 2*a* of the elongate shaft 2 into two or more different planes relative to the longitudinal axis, as shown in FIGS. 7A-7G.

Another illustrative embodiment of a handle configuration that includes a control system and is suitable for use in the suturing instruments of the invention is shown in FIGS. 10-13. In FIG. 10, the handle 1 includes an elongate housing 312, which includes a proximal end portion 314 and a distal end portion 316 and control system 310 disposed within the elongate housing 312. The elongate housing 312 further includes a first grip portion 318 and a second grip portion 320 different than the first grip portion. Each of the first grip portion 318 and second grip portion 320 is adapted to be held or grasped by a hand of a user. The elongate housing 312 (and control system 310) is couplable to the elongate shaft 2.

Figure 11:
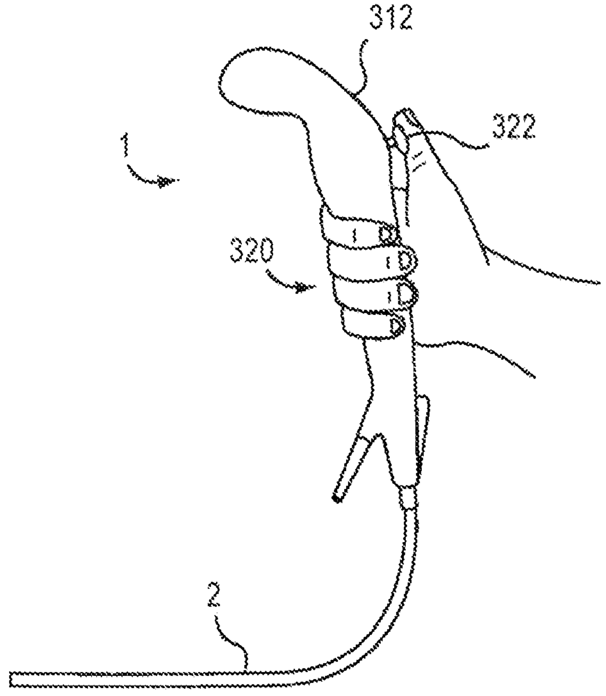
FIG. 11 depicts an alternate orientation of the handle depicted in FIG. 10.

The elongate housing 312 is adapted to be in a first orientation when the first grip portion 318 is operatively held by the hand of the user. For example, as illustrated in FIG. 11, when the user holds the elongate housing 312 of the steering mechanism 310 by the first grip portion 318, the elongate housing is in a substantially horizontal orientation. The user (e.g., a surgeon) can operate the steering button 322 with a single finger of the hand holding the first grip portion 318.

Figures 12, 13A, 13B:
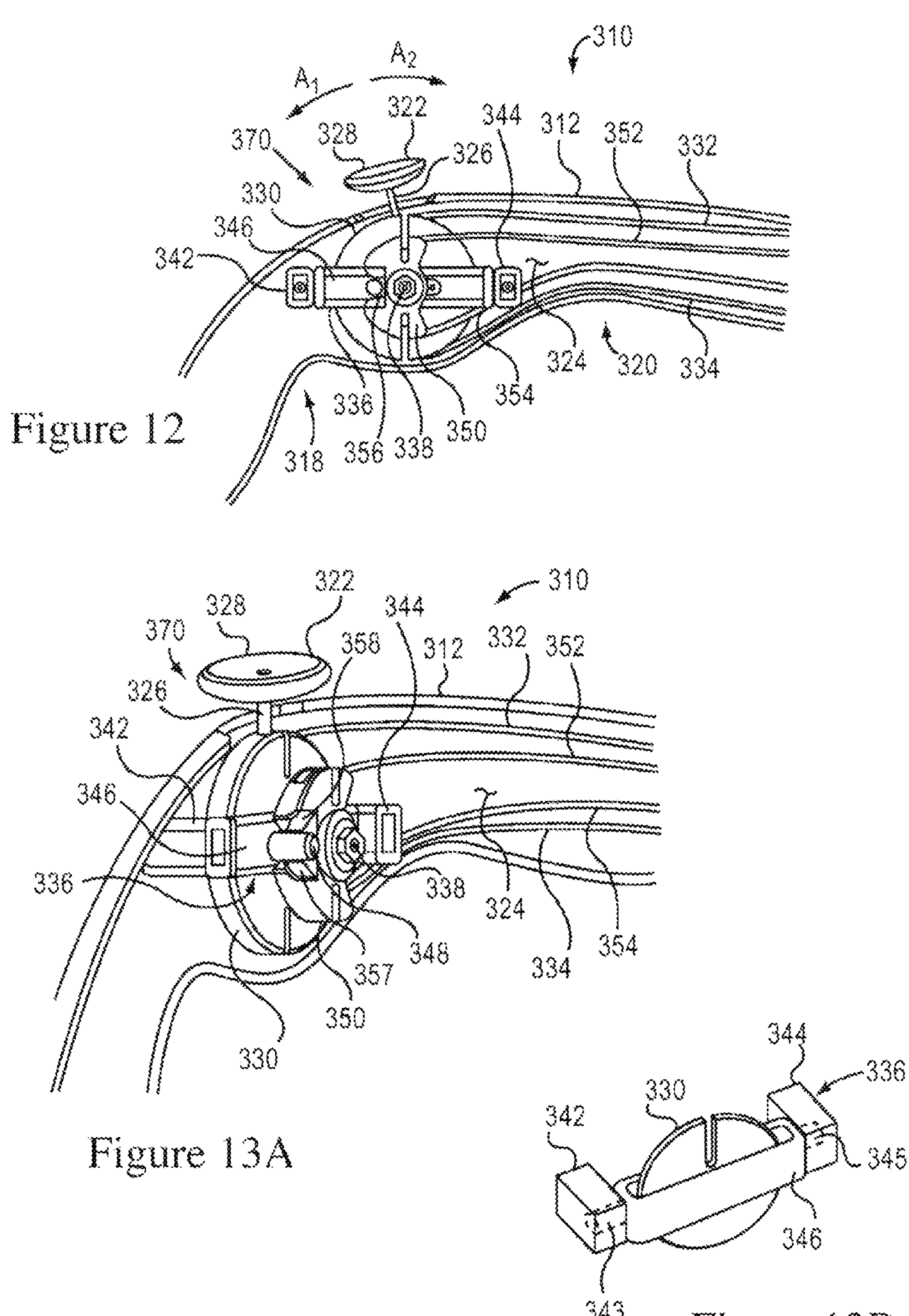
FIG. 12 is a cross-sectional view of the handle depicted in FIG. 10, illustrating the components of a control system disposed within the handle.
FIG. 13A is an alternate view of the handle depicted in FIG. 12.
FIG. 13B is an expanded view of a portion of FIG. 12.

As shown in FIG. 12 and FIG. 13, control system 310 includes the steering button 322, a first cam 330, a second cam 350, and first, second, third, and fourth wires 332, 334, 352, 354.

The first cam 330 moves in response to movement of the steering button 322. The first cam 330 is adapted to move the flexible portion of the elongate shaft 2 along the first plane when the first cam moves in response to movement of the steering button 322. As illustrated in FIG. 12, the first cam 330 is at least partially disposed in the cavity 324 of the elongate housing 312.

The first cam 330 is coupled to the elongate housing 312 by a frame 336. The frame 336 is coupled to an inner surface of the elongate housing 312 defining the cavity 324. In the embodiment illustrated in FIG. 12 and FIG. 13, the frame 336 includes a first supporting arm 342, a second supporting arm 344, and a central arm 346. The first supporting arm 342 and second supporting arm 344 are each coupled to the elongate housing 312. The central arm 346 extends between and is coupled to the first and second supporting arms 342,344.

In the embodiment illustrated in FIG. 13A, the central arm 346 defines an opening or pocket adapted to receive a portion of the first cam 330. The first cam 330 is coupled to the central arm 346. The first cam 330 can be coupled to the central arm 346 by any known coupling mechanism, including, but not limited to, a pin or other mechanical fastener.

The first cam 330 is movable with respect to the frame 336. The first cam 330 is movable between at least a first position (illustrated in FIG. 12), a second position different than the first position, and optionally a third position different from the first and second positions.

The first cam 330 is coupled to the steering button 322. In some embodiments, as illustrated in FIG. 12 and FIG. 13, the first cam 330 is fixedly coupled to the stem 326 of the steering button 322.

The first cam 330 is coupled to each of the first wire 332 and the second wire 334. As illustrated in FIG. 12 and FIG. 13, the first and second wires 332, 334 are coupled to the first cam 330 at spaced locations. The first wire 332 can be coupled to the first cam 330 proximate to the steering button 322. In the embodiment illustrated in FIG. 12, the second wire 334 is coupled to a portion of the first cam 330 different than the portion of the cam coupled to the first wire 332. The first wire 332 and the second wire 334 are each adapted to move in response to movement of the first cam 330. Additionally, the first and second wires 332,334 are each coupled to the elongate member 302 of the suturing instrument 100. Thus, movement of the first and second wires 332,334 moves the elongate shaft 2.

Referring again to FIG. 12, as the steering button 322 is moved in its first direction along a first axis (as indicated by arrow A1), the first cam 330 correspondingly moves to a second position different than its first position. As the first cam 330 moves towards its second position, the first cam moves (or pulls on) the first wire 332. The first wire 332 moves the flexible portion of the elongate shaft 2 in its first direction along the first plane (e.g., "up").

To return the elongate shaft 2 to its starting position (or the linear or relaxed position), the steering button 322 is moved in its second direction until the first cam 330 is moved (or returned) to its first position. In some embodiments, at least one of the steering button 322 and the first cam 330 is biased towards a first (or starting) position.

The handle/control systems depicted in FIGS. 8-13 are provided for illustrative purposes only and are not intended to be limiting. The handle/control system component of the suturing instruments of the invention may also include levers, knobs, robotics, a joystick, or other control features, all of which would be known to those knowledgeable about medical devices.

Now referring back to the elongate shaft 2, in certain embodiments, at least a portion of the elongate shaft 2 includes an articulation structure that provides flexibility to the articulated portion of the elongate shaft. For example, the distal portion 2*a* of the elongate shaft 2 can include an articulation structure. Alternatively, the entire elongate shaft 2 can include an articulation structure. The articulation structure can be used in conjunction with a flexible coil to provide a suturing instrument having increased flexibility and controlled maneuverability. The articulation structure can also be used as the sole means of providing flexibility to at least a portion of the elongate shaft. The articulation structure is coupled to the one or more pull wires for controllably deflecting the flexible and/or articulated portion of the elongate shaft 2. Various articulation structures that are suitable for use in the suturing devices of the invention are described in U.S. Pat. No. 7,591,783 and U.S. Patent Application Publication No. 2008/0287741, each of which is incorporated herein by reference in its entirety.

Figure 14:
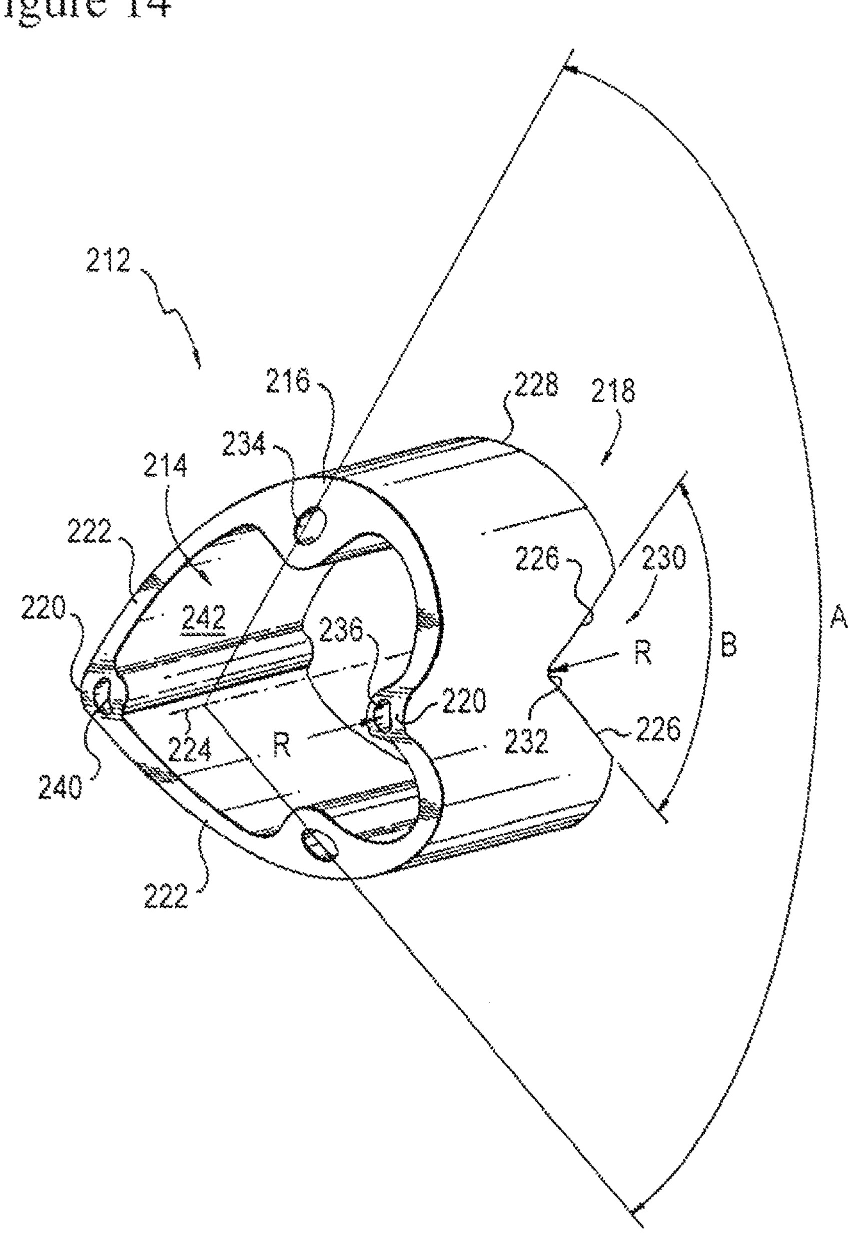
FIG. 14 depicts a link used to form an articulation structure in accordance with an embodiment of the present invention.

One embodiment of an articulation structure 200 according to the present invention is made of a series of stacked links 212 that are positioned adjacent to one another, defining an inner lumen 214 and movable with respect to each other. Referring now to FIG. 14, a link 212 according to one embodiment of the present invention includes a front face 216 and a rear face 218. Each link may be deep drawn, rolled and welded, stamped, injection molded, or otherwise formed of stainless-steel or other biocompatible material that allows the link 212 to be rigid while having a thin wall profile in order to maximize the size of the inner lumen 214.

The front face 216 of the link 212 includes a pair of oppositely arranged engagement surfaces that bisect the link 212 and define a pair of pivot points 220 that engage the corresponding rear face 218 of an adjacent link 212. The pivot points 220 are rounded over forming substantially cylindrical surfaces that serve as bearings. The front face 216 of the link 212 further includes two tapered sections 222 that are angled proximally away from the pivot point 220. The two tapered sections 222 are oriented at an angle of A0 with respect to the longitudinal axis 224 of the link 212. The terms proximal and distal require a point of reference.

In this application, the point of reference is the perspective of the user. Therefore, the term proximal will always refer to an area closest to the user, whereas distal will always refer to an area away from the user.

Similarly, the rear face 218 of the link 212 includes two sloped sections 226 that are angled distally away from a relatively flat surface 228 of the rear face 218 forming a wedge shaped recess 230 with a vertex 232 for receiving the pivot points 220 of the adjacent link 212. As with the tapered sections 222 at the front face 216 of the link, the sloped sections 226 of the rear face 218 are oriented at an angle of B0 with respect to the longitudinal axis 224. Additionally, the vertex 232 is rounded to form a substantially cylindrical surface to engage the rounded over surface of the pivot points 220.

A plurality of wire channels 234, 236, 238, 240, are integrally formed in the link 212 itself or otherwise disposed on the inner surface 242 of the link 212. The wire channels are radially spaced at predetermined distances around the circumference of the link 212. As shown in FIG. 14, channels 236 and 240 are positioned at the pivot points 220, while channels 234 and 238 are rotated 90° with respect to channels 236 and 240.

Figure 15:
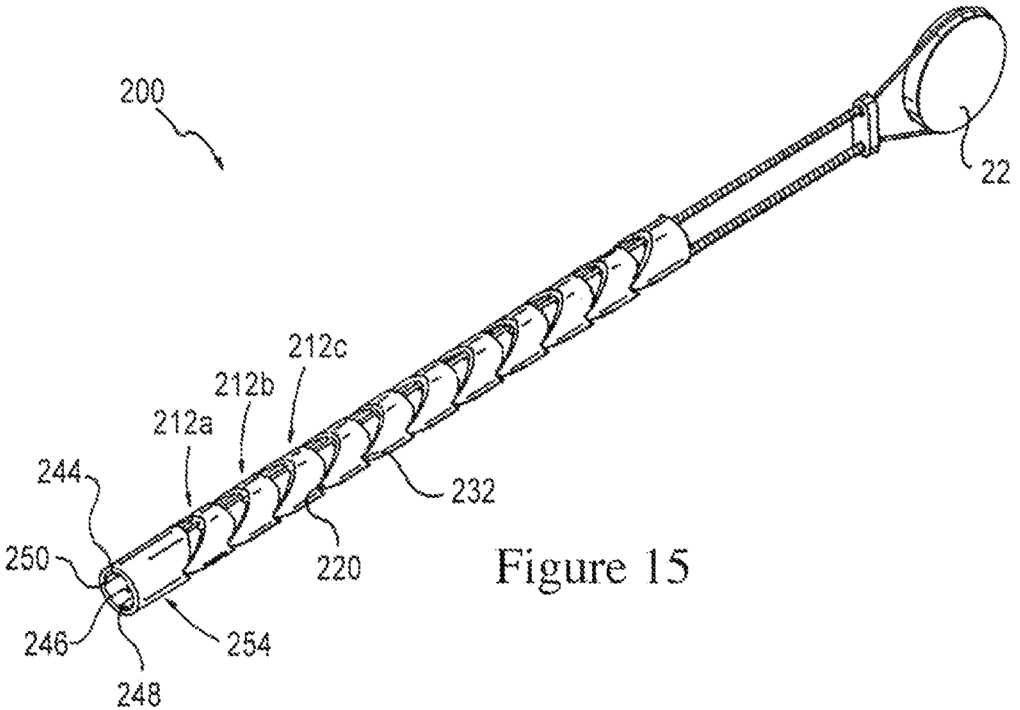
FIG. 15 depicts a schematic rendering of an articulation structure formed by stacking a series of the links shown in FIG. 14.
Figure 16:
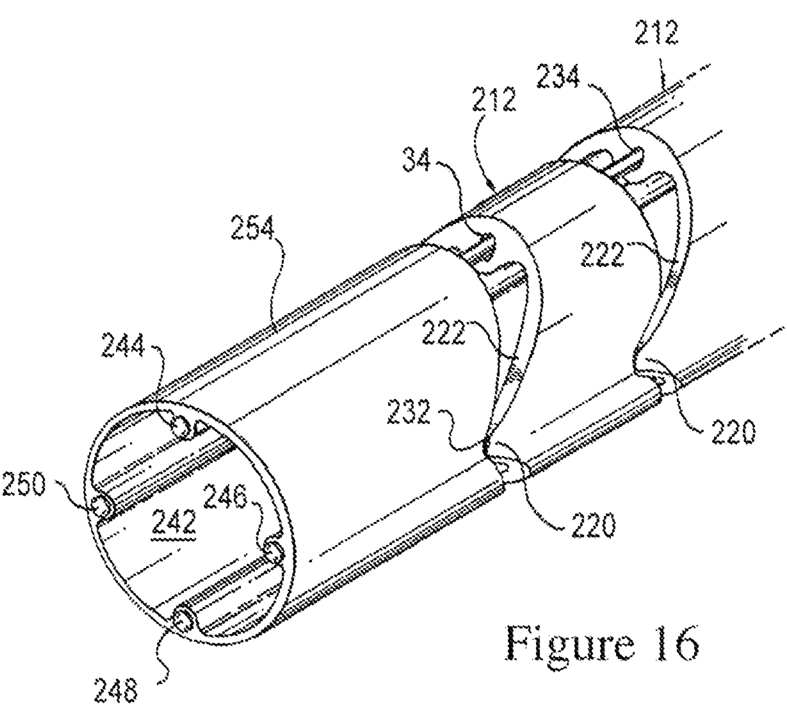
FIG. 16 depicts an enlarged portion of the articulation structure shown in FIG. 15.
Figure 17:
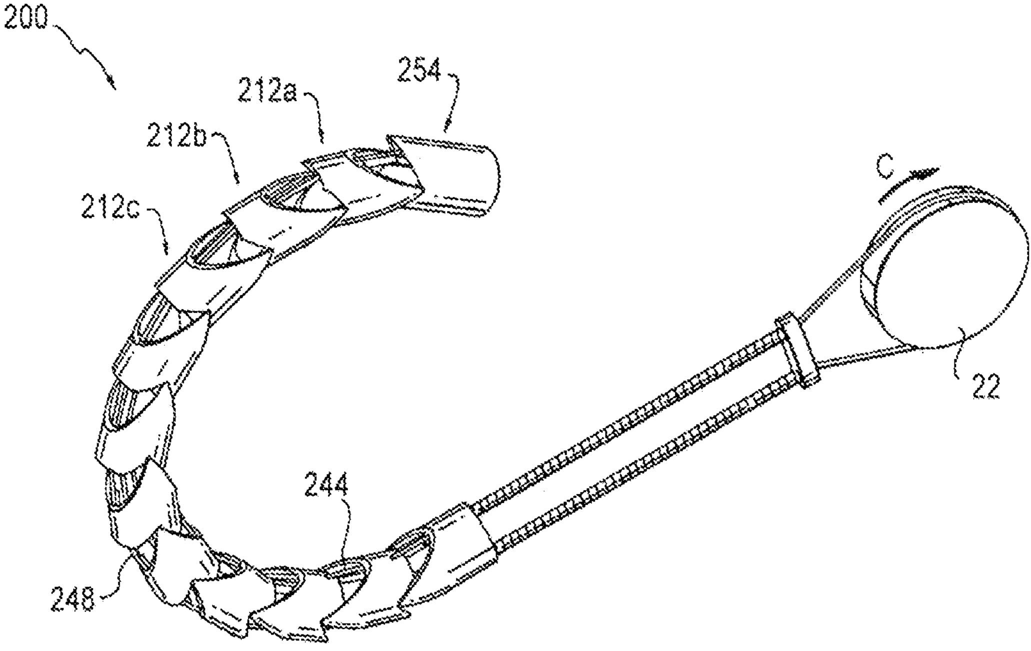
FIG. 17 depicts a schematic rendering of the articulation structure shown in FIG. 15 bent in an upward direction.

Referring now to FIGS. 15-17, the articulation structure 200 is created by stacking a number of links 212*a*, 212*b*, 212*c*, etc., such that that the pivot points 220 of each link 212 are aligned with the vertex 232 of the adjacent link 212. Locking pull-wires 246 and 250 disposed in wire channels 236 and 240 provide tension to hold adjacent links 212*a*, 212*b*, 212*c*, etc., together while the one or more pull-wires designated in FIGS. 15-17 as 244 and 248 are components of the control system for bending the articulation structure in the desired direction.

Pull wires 244 and 248 can be coupled to the control system disposed within or on handle, such as the control system 22 illustrated in FIGS. 8 and 9.

The proximal ends of pull-wires 244 and 248 can be connected to the rotatable cam in the control system 22 and the distal ends of the pull-wires 244 and 248 are connected to the distal end 254 of the articulation structure 200 (FIG. 16). As shown in FIG. 17, when the user rotates the rotatable cam in control system 22 in the clockwise direction as indicated by line C on, tension is applied to pull-wire 244, and tension is released from pull-wire 248, thereby deflecting the distal end 254 of the articulation structure in an upward direction. Conversely, when the user rotates the control cam 252 in a counter-clockwise direction, tension is applied to pull-wire 248 and released from pull-wire 244, thereby deflecting the distal end 254 in a downward direction.

The deflection capability of the articulation structure 200 is a function of the difference between angles A and Band the number of links N, which can be represented by the formula: deflection angle=(A−B)/2×(N−1). For example, in the embodiment shown in FIG. 15, if angle A is 140°, angle B is 100°, and there are 11 links including the first and last link the deflection would be 200°. The radius of deflection is a function of the angle difference and the length of the link (i.e., shorter links will produce a smaller bend radius).

Figure 18A:
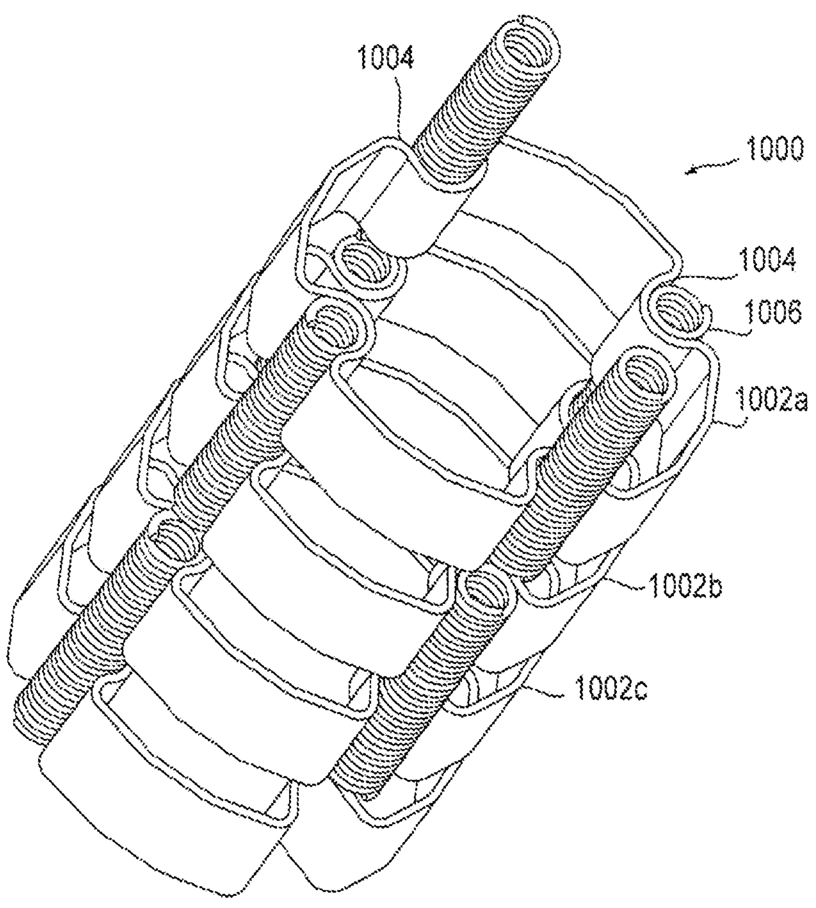
FIGS. 18A-18C illustrate alternative embodiments of an articulation structure formed of a number of stacked discs in accordance with another embodiment of the present invention.
Figure 18B:
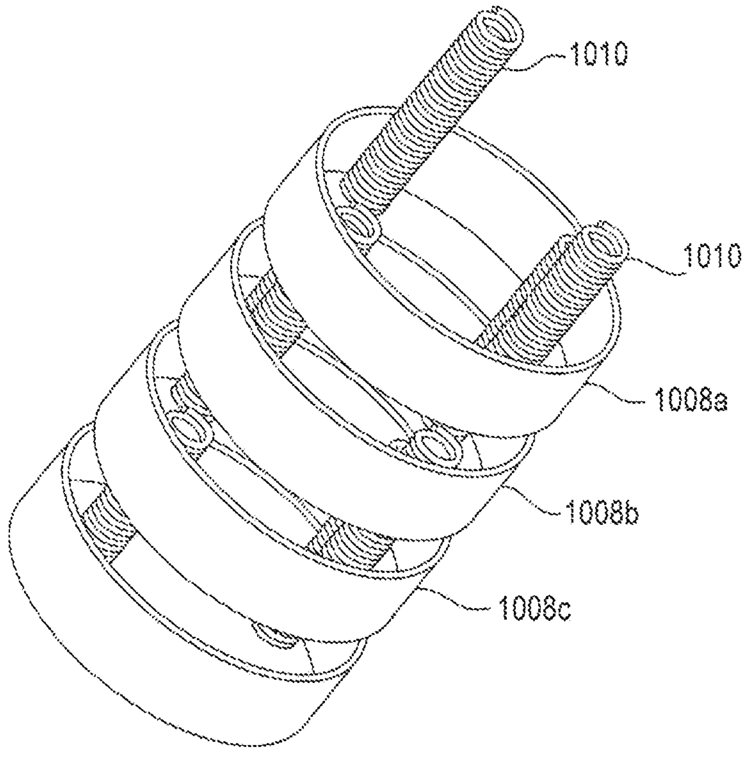
Figure 18C:
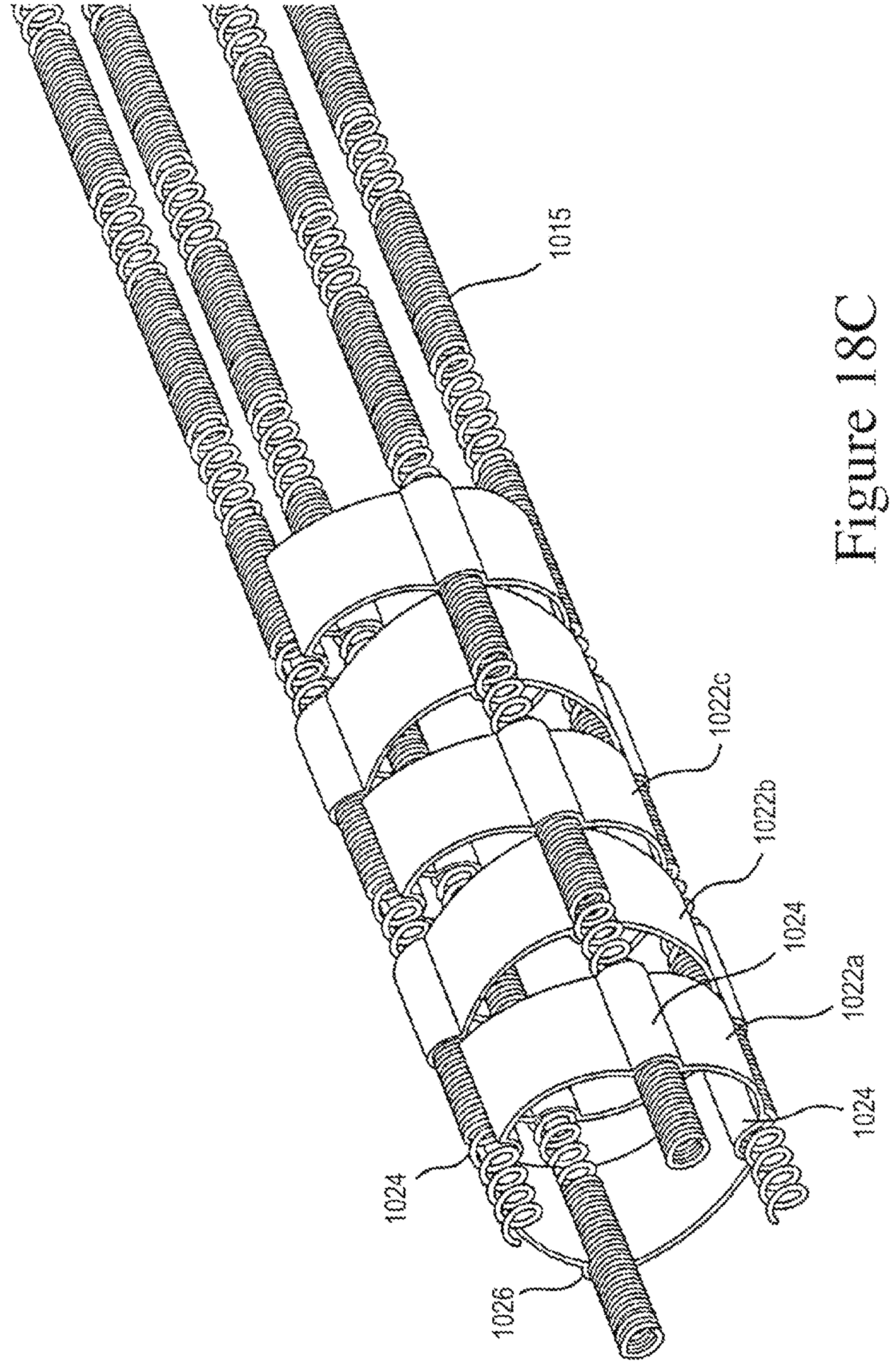

Other illustrative embodiments of an articulation structure 1000 for use in the suturing devices of the invention are depicted in FIGS. 18A-18C. Referring now to FIG. 18A, the articulation structure 1000 is made of a series of stacked rings 1002*a*, 1002*b*, 1002*c*, etc. Each ring is preferably formed of a deep-drawn steel or other metal that allows the ring to be stiff while having a thin wall profile in order to maximize the size of the inner lumen. Positioned at equal intervals around the outer circumference of the ring are inwardly extending concave recesses 1004 that receive short spring sections 1006 that are used to join adjacent rings together. Two springs on opposite sides of a ring 1002 are used to join adjacent rings together. For example, if three rings 1002*a*, 1002*b*, and 1002*c* are aligned, the rings 1002*a* and 1002*b* are joined together with spring segments located at 0° and 180° on the rings, while ring 1002*b* is joined to ring 1002*c* with orthogonally aligned spring segments located at 90° and 270° around the rings. A gap is formed between adjacent rings so that the pair of springs forms a flexible joint that can bend in directions that are the away from the longitudinal axis of the articulation structure but has limited ability to compress the articulation structure in the direction of the longitudinal axis of the articulation structure. Each spring 1006 is secured within the concave recess 1004 of the ring 1002 using an adhesive, crimping, welding, or with other securing mechanism.

In the embodiment depicted in FIG. 18A, one or more pull wires pass through the center of the spring segments and/or on the outer circumference of the articulation structure. The one or more pull wires are coupled to a control system disposed within or on handle 1 (e.g., the control system 22 depicted in FIGS. 8 and 9, or control system 310 depicted in FIGS. 10-13). As such, the articulation structure can be controllably deflected by the pull wires coupled to the control system.

FIG. 18B illustrates an alternative embodiment of the articulation structure shown in FIG. 18A. In this embodiment, the articulation structure comprises a number of deep drawn or otherwise formed metal rings 1008*a*, 1008*b*, 1008*c* that are joined together with springs that are located on the inner circumference of each ring. Each ring is connected to an adjacent ring with a pair of spring segments located on opposite sides of the ring. The springs 1010 are secured to the inner circumference of the rings 1008 with an adhesive or by welding, or using other securing means. In the embodiment shown in FIG. 18B, the one or more pull wires are routed through the spring segments and are more closely positioned to the longitudinal axis of the articulation structure. Being closer to the longitudinal axis may require more force on a pull wire to bend the articulation structure in a desired direction.

FIG. 18C shows another embodiment of an articulation joint that is similar to the articulation joint shown in FIG. 18B. However, in this embodiment, the articulation joint is comprised of a number of rings 1022*a*, 1022*b*, 1022*c* having oppositely arranged concave recesses 1024 and convex recesses that allow a spring 1015 having alternate tightly and loosely wound segments to pass on the outside of one ring and on the inside of an adjacent ring in an alternating fashion. The oppositely arranged convex and concave recesses allow a spring to be secured to the ring with an adhesive, welding, or other bonding mechanism.

Although the discs of the articulation structures described herein are generally circular in shape, it will be appreciated that other shapes could be used.

The embodiments of flexible and/or articulated suturing instruments described herein are provided for illustrative purposes only and are not intended to be limited. Additional deflection sections and/or pull-wires could be included in the elongate shaft of the suturing instrument and/or the control system, depending on how many planes of deflection are desired.

The suturing instrument's component materials should be biocompatible. For example, the handle 1, the elongate shaft 2, and portions of the suturing head 3 and needle deployment system, or portions thereof, may be fabricated from extruded, molded, or machined plastic material(s), such as polypropylene, polycarbonate, or glass-filled polycarbonate. Other components, for example the needle 6, may be made of stainless steel. Preferably, the pull-wires are made from stainless steel, polymer filaments, strong textile or synthetic material such as Kevlar® or nylon, or other metals and alloys such as, for example, Nitinol™, which is a nickel-titanium alloy. Other suitable materials will be apparent to those skilled in the art. The material(s) used to form the suture should be biocompatible. The surgeon will select the length, diameter, and characteristics of the suture to suit a particular application. Additionally, the mechanical components and operation are similar in nature to those disclosed in U.S. Pat. Nos. 5,364,408, 5,575,800, 6,048,351, and 6,346,111, and commonly owned U.S. application Ser. No. 10/210,984 (published as U.S. Patent Application Publication No. 2004/0034372), each of which is incorporated by reference herein in its entirety.

Certain embodiments according to the invention have been disclosed. These embodiments are illustrative of, and not limiting on, the invention. Other embodiments, as well as various modifications and combinations of the disclosed embodiments, are possible and within the scope of the disclosure.

What is claimed is:

1. A suturing instrument, comprising a handle having a housing defining a cavity;

an elongate shaft extending from the handle, at least a portion of the elongate shaft being flexible;

one or more pull wires extending from the handle into the flexible portion of the elongate shaft for deflecting the flexible portion of the elongate shaft;

a steering button extending from the housing and operatively coupled to a cam, the cam being disposed within a pocket of a frame member, the frame member being disposed within the cavity of the housing; and a suturing head extending from a distal end of the elongate shaft, the suturing head comprising a needle carrier channel, a needle carrier configured to releasably hold a needle, and a needle catch, the needle carrier being movably disposed within the needle carrier channel.

2. The suturing instrument of claim 1, wherein the needle carrier moves along the needle carrier channel out of the suturing head into an extended position, and back into the suturing head into a retracted position.

3. The suturing instrument of claim 2, further comprising a needle deployment system at least partially disposed within the elongate shaft and coupled to the needle carrier for moving the needle carrier between the extended position and the retracted position.

4. The suturing instrument of claim 3, wherein the needle deployment system moves the needle carrier out of the suturing head in a semi-circular path towards the needle catch such that the needle held by the needle carrier is released from the needle carrier and retained in the needle catch.

5. The suturing instrument of claim 3, wherein the handle includes an actuating mechanism coupled to the needle deployment system for actuating the needle deployment system.

6. The suturing instrument of claim 1, wherein the cam is a rotatable cam coupled to the one or more pull wires.

7. The suturing instrument of claim 1, wherein the elongate shaft is capable of being deflected into multiple different planes relative to a longitudinal axis of the elongate shaft.

8. The suturing instrument of claim 1, wherein the elongate shaft comprises a flexible coil.

9. The suturing instrument of claim 8, wherein the flexible coil comprises a Bowden coil.

10. The suturing instrument of claim 8, wherein the elongate shaft further includes an outer sleeve disposed on the outside of the flexible coil to provide a smooth exterior surface.

11. The suturing instrument of claim 1, wherein at least a portion of the elongate shaft includes an articulation structure.

12. The suturing instrument of claim 11, wherein the flexible portion of the elongate shaft includes the articulation structure.

13. The suturing instrument of claim 11, wherein the articulation structure comprises a series of stacked links disposed adjacent to one another and movable with respect to each other, each link including a front face tapered to a pair of pivot points and a rear face defining a wedge shaped recess for receiving the pivot points of the adjacent link, and wherein said one or more pull-wires are configured for providing tension to the articulation structure and holding the adjacent links together.

14. The suturing instrument of claim 11, wherein the articulation structure comprises:

a first articulation section, the first articulation section includes a first series of stacked links disposed adjacent to one another and movable with respect to each other, each link including a front face tapered to a pair of pivot points and a rear face defining a wedge shaped recess for receiving the pivot points of the adjacent link;

a second articulation section, the second articulation section includes a second series of stacked links disposed adjacent to one another and movable with respect to each other, each link including a front face tapered to a pair of pivot points and a rear face defining a wedge shaped recess for receiving the pivot points of the adjacent link, the wedge shaped recesses of the first articulation section radially offset from the wedge shaped recesses of the second articulation section;

wherein said one or more pull wires are configured for providing tension to the articulation structure and holding the adjacent links together.

15. The suturing instrument of claim 11, wherein said articulation structure comprises:

a number of ring links, each having an inner circumference and an outer circumference, each ring link including:

two concave recesses with openings that face radially outward from the outer circumference of the ring link that are positioned on opposite sides of the outer circumference of the ring link; and two concave recesses with openings that face radially inward from the inner circumference of the ring link that are positioned on opposite sides of the inner circumference of the ring link and are oriented at 90 degrees to the two concave recesses positioned on opposite sides of the outer circumference of the ring link; and a plurality of spring segments that are secured within the concave recesses on the outer circumferences and inner circumferences of the ring links to join adjacent ring links together and that are bendable in the articulating joint;

wherein the concave recesses on the outer circumference of a given ring link are aligned with the concave recesses on the inner circumference of an adjacent ring link in the articulating joint.

16. The suturing instrument of claim 15, wherein the spring segments define apertures adapted to receive the one or more pull wires therethrough.

17. A suturing instrument, comprising a handle including a control system, the handle including a housing defining a cavity;

an elongate shaft extending from the handle, the elongate shaft including a distal portion, at least a portion of the elongate shaft being flexible;

one or more pull wires extending from the handle into the distal portion of the elongate shaft, the one or more pull wires coupled to the control system to allow active control of the flexible portion of the elongate shaft, the control system including a cam disposed within a pocket of a frame member, the frame member being disposed within the cavity of the housing; and a suturing head extending from a distal end of the distal portion of the elongate shaft, the suturing head comprising a needle carrier channel, a needle carrier configured to releasably hold a needle, and a needle catch, the needle carrier being movably disposed within the needle carrier channel.

18. A suturing instrument, comprising a handle having a housing defining a cavity;

an elongate shaft extending from the handle, the elongate shaft including a distal portion, at least a portion of the shaft being flexible and including an articulation structure;

one or more pull wires extending from the handle into the distal portion of the elongate shaft for deflecting the articulated portion of the elongate shaft; and a steering member extending from the housing and operatively coupled to a cam, the cam being disposed within a pocket of a frame member, the frame member being disposed within the cavity of the housing; and a suturing head extending from a distal end of the distal portion of the elongate shaft, the suturing head comprising a needle carrier channel, a needle carrier configured to releasably hold a needle, and a needle catch, the needle carrier being movably disposed within the needle carrier channel.

* * * * *